United States Patent [19]

Clark

[11] 4,353,901
[45] Oct. 12, 1982

[54] 9-(1,4-BENZODIOXAN-2-YLALKYL AND HYDROXYALKYL)-1-OXA-4,9-DIAZAS-PIRO[5.5]UNDECAN-3-ONES

[75] Inventor: Robin D. Clark, Palo Alto, Calif.
[73] Assignee: Syntex (U.S.A.) Inc., Palo Alto, Calif.
[21] Appl. No.: 312,447
[22] Filed: Oct. 19, 1981
[51] Int. Cl.³ ............... C07D 498/10; A61K 31/535
[52] U.S. Cl. ............................. 424/248.57; 544/71
[58] Field of Search .................. 544/71; 424/248.57
[56] References Cited

U.S. PATENT DOCUMENTS 3,577,425  5/1971  Nakanishi et al. ................ 424/267
3,720,670  3/1973  Nakanishi et al. ................ 544/71

FOREIGN PATENT DOCUMENTS 47-35435  9/1972  Japan .

OTHER PUBLICATIONS

Chemical Abstracts, vol. 81: 33153c, (1974).

*Primary Examiner*—Norma S. Milestone
*Attorney, Agent, or Firm*—Annette M. Moore; Tom M. Moran

[57] ABSTRACT

Compounds useful in the prevention and/or treatment of hypertension, congestive heart failure, arrhythmia, migraine, vasospastic disorders, and asthma are represented by the formula:

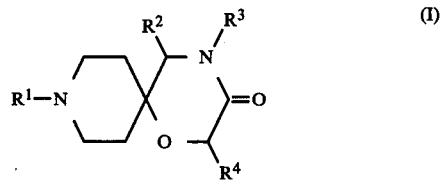

wherein:
$R^1$ is

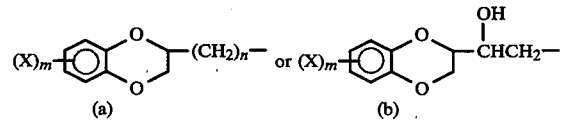

$R^2$, $R^3$, and $R^4$ are independently hydrogen or lower alkyl of one to four carbon atoms;
X is hydrogen, lower alkyl of one to four carbon atoms, lower alkoxy of one to four carbon atoms or halo;
m is 1 or 2; and
n is 1, 2 or 3; and
the pharmaceutically acceptable acid addition salts thereof.

15 Claims, No Drawings

9-(1,4-BENZODIOXAN-2-YLALKYL AND HYDROXYALKYL)-1-OXA-4,9-DIAZASPIRO[5.5]UNDECAN-3-ONES

BACKGROUND OF THE INVENTION

1. Field of the Invention

This invention relates to 9-(1,4-benzodioxan-2-ylalkyl and hydroxyalkyl)-1-oxa-4,9-diazaspiro[5.5]-undecan-3-ones and the pharmaceutically acceptable acid addition salts thereof which are useful in the prevention and/or treatment of cardiovascular diseases such as hypertension, congestive heart failure, arrhythmia, migraine, and vasospastic disorders, as well as asthma. The invention also relates to a pharmaceutically acceptable composition containing an effective amount of at least one of the compounds in combination with a suitable excipient, the composition being useful for the prevention and/or treatment of cardiovascular diseases such as hypertension, congestive heart failure, arrhythmia, migraine, and vasospastic disorders, as well as asthma in mammals. The invention also relates to a process for making the compounds of the invention.

2. Related Disclosures

Certain benzodioxanylalkyl oxadiazaspiro-decanes and undecanes are known. See, for example, U.S. Pat. Nos. 3,577,425 and 3,720,670 and Japanese Pat. No. 7,235,435. See also Chimie Therapeutique, July-August 1973, 4, 393. A novel class of (1,4-benzodioxan-2-ylalkyl and hydroxyalkyl)-oxadiazaspiroundecanes has now been prepared.

SUMMARY OF THE INVENTION

The first aspect of this invention is the group of compounds represented by the formula:

(I) [structure]

wherein: $R^1$ is (a) [structure] $(X)_m$-benzodioxan-$(CH_2)_n$- or (b) $(X)_m$-benzodioxan-CHCH$_2$- with OH $R^2$, $R^3$, and $R^4$ are independently hydrogen or lower alkyl of one to four carbon atoms;

X is hydrogen, lower alkyl of one to four carbon atoms, lower alkoxy of one to four carbon atoms or halo;

m is 1 or 2; and n is 1, 2 or 3; and the pharmaceutically acceptable acid addition salts thereof.

Another aspect of the invention is a composition useful in the prevention and/or treatment of cardiovascular diseases such as hypertension, congestive heart failure, arrhythmia, migraine, and vasospastic disorders as well as asthma in mammals which composition comprises an effective amount of at least one compound chosen from those represented by formula (I) above or a pharmaceutically acceptable acid addition salt thereof and a pharmaceutically suitable excipient.

Still another aspect of the invention is a method for preventing and/or treating cardiovascular diseases such as hypertension, congestive heart failure, arrhythmia, migraine, and vasospastic disorders as well as asthma in mammals which comprises administering an effective amount of at least one compound chosen from those represented by formula (I) above.

Still another aspect of the invention is a process for preparing a compound of formula (I) above which comprises reacting a compound of the formula:

(VIII) [structure]

wherein: $R^2$, $R^3$, and $R^4$ are as defined above with a reactive intermediate of the formula:

(IX) [structure with $(X)_m$ and $(CH_2)_n Y$]

wherein: $R^2$, $R^3$, $R^4$, X, m and n are as defined above and Y is a leaving group, e.g., halo such as chloro, bromo or iodo, or a sulfonate ester, e.g., p-toluenesulfonate or methanesulfonate; or with a suitable benzodioxanylepoxide of the formula:

(X) [structure with $(X)_m$ and CHCH$_2$ epoxide]

wherein: X is as defined above.

The compound of formula (I) may be further reacted with an acid (infra) to form the acid addition salt thereof, or the salt of a compound of formula (I) may be reacted with a base to form compounds of formula (I), or one salt may be converted to a second salt of compound of formula (I).

DETAILED DESCRIPTION AND PREFERRED EMBODIMENT

The broadest aspect of the present invention is the group of compounds represented by the formula:

(I) [structure with numbered positions 1,2,3,4,5,6,7,8,9,10,11]

wherein: $R^1$ is:

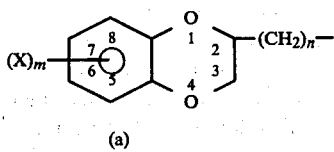

(a)

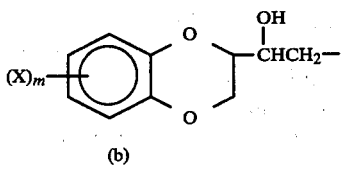

(b)

$R^2$, $R^3$, and $R^4$ are independently hydrogen or lower alkyl of one to four carbon atoms;

X is hydrogen, lower alkyl of one to four carbon atoms, lower alkoxy of one to four carbon atoms or halo;

m is 1 or 2; and n is 1, 2 or 3; and the pharmaceutically acceptable acid addition salts thereof.

When $R^1$ is:

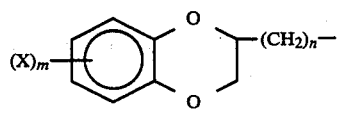

the preferred group of compounds are those wherein X is hydrogen and n is 1 or 2, with 2 being most preferred.

When $R^1$ is:

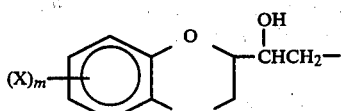

it is preferred that X is hydrogen. The erythro isomer is preferred.

A preferred group of compounds of formula (I) is that wherein $R^4$ is hydrogen and $R^2$ and $R^3$ are independently hydrogen or lower alkyl. Within the above group preferred compounds are those wherein $R^2$ is methyl or ethyl and $R^3$ is hydrogen. A still more preferred group of compounds of formula (I) is that wherein $R^2$ is hydrogen and $R^3$ is methyl, ethyl or propyl. The most preferred subgroup of compounds is that wherein $R^2$, $R^3$ and $R^4$ are independently hydrogen.

As used in the specification and the appended claims, unless specified to the contrary, the following terms have the meaning indicated. The term "lower alkyl" refers to a straight or branched chain monovalent substituent consisting solely of carbon and hydrogen, containing no unsaturation and having from one to four carbon atoms. Examples of lower alkyl groups are methyl, ethyl, n-propyl, i-propyl, n-butyl, i-butyl, s-butyl and t-butyl. The term "lower alkoxy" refers to a monovalent substituent containing oxygen and of the formula "lower alkyl-O-" wherein lower alkyl is as defined above. Examples of lower alkoxy groups are methoxy, ethoxy, n-propoxy i-propoxy, n-butoxy, i-butoxy, s-butoxy and t-butoxy. The term "halo" refers to fluoro, bromo and chloro. The term "pharmaceutically acceptable acid addition salts" refers to salts of the subject compounds which possess the desired pharmacological activity and which are neither biologically nor otherwise undesirable. These salts are formed with inorganic acids such as hydrochloric acid, hydrobromic acid, sulfuric acid, nitric acid or phosphoric acid; or organic acids such as acetic acid, propionic acid, glycolic acid, pyruvic acid, oxalic acid, malonic acid, succinic acid, malic acid, maleic acid, fumaric acid, tartaric acid, citric acid, benzoic acid, cinnamic acid, mandelic acid, methansulfonic acid, ethanesulfonic acid, p-toluenesulfonic acid and the like.

The compounds of the present invention are named according to the IUPAC nomenclature system. The locants for the substituents on the ring systems of the compounds of the instant invention are as depicted above. For example, when $R^1$ is group (a), X is methyl, $R^2$, $R^3$ and $R^4$ are hydrogen, m is 1 and n is 2, the compound of formula (I) is named as 9-[2-(6-methyl-1,4-benzodioxan-2-yl)ethyl]-1-oxa-4,9-diazaspiro[5.5]undecan-3-one.

The compounds of formula (I) wherein $R^1$ is group (b) exist as erythro and threo isomers. Accordingly, the compounds of the present invention wherein $R^1$ is group (b) may be prepared in either the erythro or threo form or as a mixture. Unless specified, the compounds of the instant invention wherein $R^1$ is group (b) are a mixture. However, the scope of the subject invention is not considered limited to the erythro-threo mixture but to encompass the individual isomers of the subject compounds.

The pure erythro or threo isomers may be prepared by reacting the erythro or threo isomer of the intermediate of formula (X) (infra) or by the method described hereinafter. If desired, a mixture of the intermediates used to prepare compounds of formula (I) wherein $R^1$ is group (b) or the final product may be separated by, e.g., recrystallization and chromatography. It is preferred to prepare the individual isomers from the isomeric intermediates of formula (X).

Certain compounds of formula (I) wherein $R^2$ and $R^3$ are lower alkyl may have geometric(cis and trans) isomers. The geometric isomers may be separated by various methods, for example, selective crystallization and column chromatography. Alternatively, where, appropriate, the intermediates of formula (VIII) (infra) may be separated and converted to the final cis or trans isomers of compounds of formula (I). Both geometric isomers as well as mixtures thereof are intended to be included within the scope of the present invention.

Compounds of formula (I) also exist as optical isomers because the spiro ring group does not possess a plane of symmetry. Accordingly, the compounds of the present invention may be prepared in either optically active form, or as a racemic mixture. Unless otherwise specified, the compounds described herein are all in the racemic form. However, the scope of the subject invention herein is not to be considered limited to the racemic form but to encompass the individual optical isomers of the subject compounds.

If desired, racemic intermediates of formula (VIII) (infra) or final products prepared herein may be resolved into their optical antipodes by conventional resolution means known per se, for example, by the separation (e.g., fractional crystallization) of the diastereomeric salts formed by reaction of, e.g., racemic compounds of formula (I) or the intermediate of formula (VIII) (infra) with an optically active acid. Exemplary of such optically active acids are the optically active forms of camphor-10-sulfonic acid, α-bromocamphor-π-sulfonic acid, camphoric acid, menthoxyacetic acid, tartaric acid, malic acid, diacetyltartaric acid, pyrrolidone-5-carboxylic acids, and the like. The separated pure diastereomeric salts may then be cleaved by standard means to afford the respective optical isomers of the compounds of formula (I) or the intermediate of formula (VIII) (infra).

ADMINISTRATION AND FORMULATION

Another aspect of the present invention relates to pharmaceutical compositions useful in the prevention and/or treatment of cardiovascular diseases such as hypertension, congestive heart failure, arrhythmia, migraine, and vasospastic disorders, as well as asthma, particularly in the prevention and/or treatment of hypertension in a mannalian subject, comprising a compound of formula (I), or a pharmaceutically acceptable acid addition salt thereof, in admixture with a pharmaceutically acceptable non-toxic carrier. Useful pharmaceutical carriers for the preparation of the pharmaceutical compositions hereof can be solids or liquids. Thus, the compositions can take the form of tablets, pills, capsules, powders, sustained release formulations, solutions, suspensions, elixirs, aerosols, and the like. Carriers can be selected from the various oils, including those of petroleum, animal, vegetable or synthetic origin, for example, peanut oil, soybean oil, mineral oil, sesame oil, and the like. Water, saline, aqueous dextrose, and glycols are preferred liquid carriers particularly for injectable solutions. Suitable pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk, glycerol, propylene glycol, water, ethanol, and the like. Suitable pharmaceutical carriers and their formulations are described in "Remington's Pharmaceutical Sciences" by E. W. Martin. Such compositions will, in any event, contain a therapeutically effective amount of the active compound together with a suitable amount of carrier so as to prepare the proper dosage form for proper administration to the subject. Thus, the level of the drug in the formulation can vary from 5 percent weight (%W) to 95%W of the drug based on the total formulation and about 5%W to 95%W excipient. Preferably the drug is present at a level of 10%W to 70%W.

Another aspect of the present invention relates to a method for preventing and/or treating cardiovascular diseases such as hypertension, congestive heart failure, arrhythmia, migraine, and vasospastic disorders as well as asthma in a mammalian subject comprising administering a therapeutically effective amount of a compound of formula (I), or a pharmaceutically acceptable acid addition salt thereof.

In the practice of the above described methods of the present invention a therapeutically effective amount of the compound of formula (I) or a pharmaceutical composition containing same is administered via any of the usual and acceptable methods known in the art, either singly or in combination with another compound or compounds of the present invention or other pharmaceutical agents. These compounds or compositions can thus be administered orally, systemically (i.e., intranasally, or by suppository) or parenterally (i.e., intramuscularly, subcutaneously and intravenously), and can be administered either in the form of solid or liquid dosages including tablets, solutions, suspensions, aerosols, and the like, as discussed in more detail hereinabove.

The formulation can be administered in a single unit dosage form for continuous treatment or prevention or in a single unit dosage form ad libitum when relief of symptoms is specifically required.

In view of the foregoing as well as in consideration of the degree of severity of the condition being treated, age of subject and so forth, all of which factors are determinable by routine experimentation by one skilled in the art, the effective dosage in accordance herewith can vary over a wide range. Generally, a therapeutically effective amount ranges from about 0.01 to about 5 mg./kg. body weight per day and preferably, for example, for antihypertensive use, from about 1 to about 3 mg./kg. body weight per day. In alternative terms, for an average 70 kg. adult human subject, a therapeutically effective amount in accordance herewith would be, in preferred embodiments from about 7 mg. to about 120 mg. per day per subject.

PROCESS OF THE INVENTION

Compounds of formula (I) are prepared by the reaction sequence shown below:

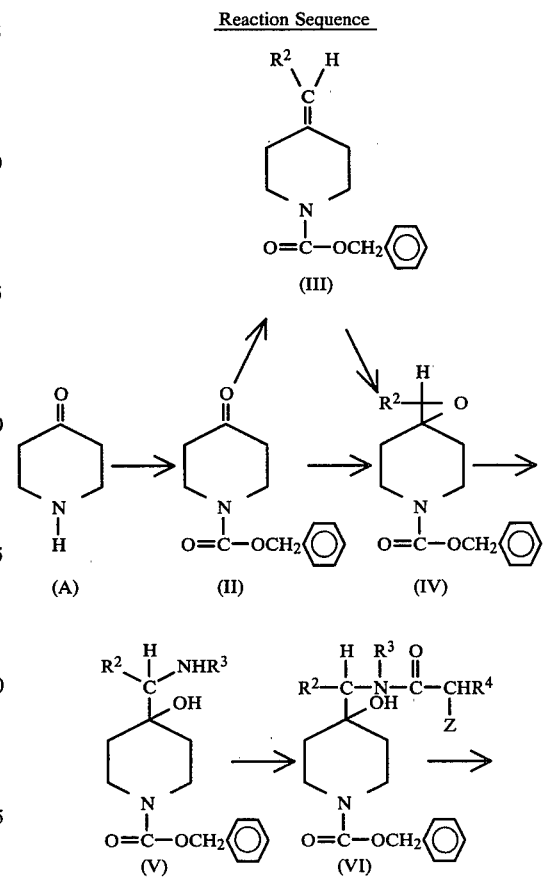

-continued
Reaction Sequence

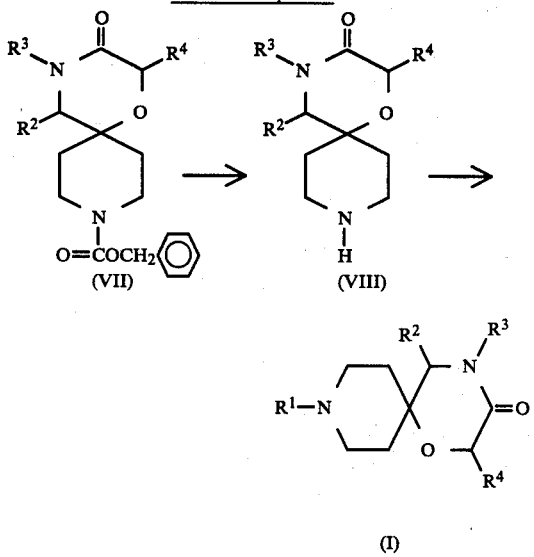

wherein $R^1$, $R^2$, $R^3$, and $R^4$ are as defined above and Z is chloro, bromo or iodo.

In the above sequence, 4-piperidone(A), available from, i.a., Aldrich Chemical Co., is reacted with benzyl chloroformate, also available from, i.a., Aldrich Chemical Co., by the method described in *Organic Chemistry*, by Robert T. Morrison and Robert N. Boyd, 2nd Edition, Ch. 37, p. 1112 to yield the N-protected-4-piperidone of formula (II). Typically, the reaction is carried out in a solvent such as water and is cooled to a temperature of about 0° C. to about 25° C., preferably from about 5° C. to about 15° C. for 3 hours to 24 hours, preferably 6 hours to 12 hours. The 4-piperidone is in a molar ratio of 0.7 to 0.8 mole to 1 mole of benzyl chloroformate, particularly in a molar ratio of 0.75 mole of 4-piperidone to 1 mole of benzyl chloroformate.

The N-protected piperidine epoxide of formula (IV) wherein $R^2$ is hydrogen is prepared by the method described in J. Am. Chem. Soc., 81, 1353 (1965). N-protected piperidone, dispersed or dissolved in an inert aprotic solvent such as dimethyl sulfoxide, tetrahydrofuran and the like is reacted with an ylid formed by the reaction of trimethyl sulfonium or trimethyl sulfoxonium iodide with an alkali metal hydride such as sodium hydride. Typically, the reactants, in a molar ratio of from 1 to 2 moles, preferably from 1.3 to 1.6 moles of ylid to 1 mole of N-protected-4-piperidone, are stirred at a temperature of between 0° C. to 30° C., preferably at room temperature for about 10 hours to 24 hours, preferably for about 12 hours to 18 hours. This is followed by heating at 40° C. to about 100° C., preferably from about 50° C. to 60° C., for 15 minutes to about 2 hours, preferably for about 45 minutes to about 1.5 hours.

The epoxides of formula (IV) wherein $R^2$ is lower alkyl are prepared by first preparing the olefin of formula (III) then epoxidizing the olefin by methods well known in the art such as by the catalytic oxidation of the C—C double bond with air or by peroxidation of the C—C double bond with a peroxy acid such as peroxybenzoic acid. The compounds of formula (III) are prepared by the well known Wittig reaction in which N-protected piperidone is reacted with a methylenetriphenylphosphorane ylid of the formula $Ph_3P=CHR^2$ wherein $R^2$ is as defined above. The ylid is prepared by reacting triphenylphosphine with an $R^2CH_2$ halide wherein $R^2$ is as defined above followed by reaction with an organolithium compound such as phenyllithium or n-butyllithium. The reaction conditions for the preparation of the ylid and the olefin are thoroughly discussed in "The Wittig Reaction" by Adalbert Maercker in *Organic Reaction* V. 14, Ch. 3, p. 270 (1965).

The epoxide ring of compounds of formula (IV) is readily opened at elevated temperatures by any $R^3$-substituted amine wherein $R^3$ is as defined above forming 1-carbobenzoxy-4-hydroxy-4-($R^3$-aminomethyl)piperidine of formula (V). Typically, the reactants are heated at a temperature of between about 75° C. to about 175° C., preferably from about 100° C. to about 125° C. for about 3 hours to about 24 hours, preferably for about 3 hours to about 6 hours. The reaction is typically conducted in a solution of the $R^3$-substituted amine such as ammonia, methylamine, ethylamine and the like in an alcohol such as methanol and the like at a molar ratio of N-protected piperidine epoxide to amine of 1 mole to 50 moles, preferably of 1 mole to 20 moles.

The hydroxy amine compounds of formula (V) are reacted with an α-chloroacid chlorides such as α-chloroacetyl chloride, α-chloropropionyl chloride, α-chloro-n-butryl chloride and the like in a polar aprotic solvent such as ethyl acetate, tetrahydrofuran, dimethyl formamide and the like optionally followed by reaction with an alkali metal iodide such as sodium iodide to yield compounds of formula (VI) wherein Z is chloro, bromo or iodo. The reaction is run in the presence of a suitable acid acceptor such as trimethylamine, triethylamine, an alkali metal carbonate such as sodium or potassium carbonate and the like at a temperature from about 0° C. to about 25° C., preferably from about 5° C. to about 10° C.

The α-chloroacid chlorides which are not readily available may be prepared by conventional methods such as the Hell-Volhard-Zelinsky Reaction in which the appropiate acid is reacted with chlorine in the presence of phosphorus. See, for example, *Organic Chemistry* by Robert T. Morrison and Robert N. Boyd, 2nd Edition, Ch. 18, p. 604 and Chem. Revs. 7, 180 (1930).

Cyclization of compounds of formula (VI) is carried out by contacting compounds of formula (VI) with a strong base such as an alkali metal alkoxide dissolved in an alcohol (e.g. potassium t-butoxide in t-butyl alcohol) in a polar aprotic solvent such as tetrahydrafuran, dimethylformamide and the like. The mixture is refluxed for about 0.1 hour to about 1 hour, preferably for about 0.1 hour to about 0.2 hour.

The compounds of formula (VII) are treated with hydrogen bromide in acetic acid to remove the N-protecting group to yield compounds of formula (VIII).

The intermediates of formula (IX), wherein Y is halo, are readily prepared by reacting a solution or dispersion of the unsubstituted or substituted 1,4-benzodioxan-2-ylalkanol with a phosphorus trihalide, a triphenyl phosphine halogen adduct or a triphenoxyphosphorus alkyl halide. The reaction is typically carried out in an inert reaction medium such as dimethylformamide, diethylether and the like from about room temperature to about 100° C. using an excess of a halogenating agent, e.g., 1.1 to 3.0 times the molar equivalence of the 1,4-benzodioxan-2-ylalkanol. The 1,4-benzodioxan-2-ylalkyl halide intermediate is preferably isolated before being used in the reaction with compounds of formula (VIII), the isolation being accomplished by conventional means such as distillation, crystallization or chromatography.

The sulfonate esters of formula (IX) may be prepared by the standard procedure of treating the alcohol with an excess of, for exapmle, methanesulfonyl chloride or p-toluenesulfonyl chloride, in the presence of a base, for example, pyridine or triethylamine. The reaction is carried out at a temperature from about −20° to +50° C., preferably between about 0° and 20° C.

The compounds of the instant invention wherein $R^1$ is

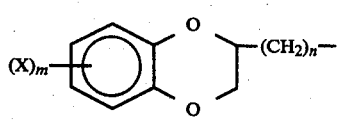

wherein X, m and n are as defined above are prepared by treating the intermediate of formula (IX), wherein Y is a leaving group, with the compound of formula (VIII) in the presence of the acid acceptor in an inert organic solvent such as dimethylformamide, tetrahydrofuran and the like at a temperature from about −10° C. to 120° C., preferably from about 50° C. to about 100° C. for about 6 hours to about 48 hours, preferably from about 16 hours to about 18 hours. Effective acid acceptors are organic bases such as trialkyl amines, e.g., trimethylamine, triethylamine and quinuclidine and inorganic bases such as alkali metal carbonates, for example, sodium carbonate or potassium carbonate and alkali metal hydroxide such as sodium hydroxide, potassium hydroxide and the like.

Compounds of formula (I) wherein $R^1$ is

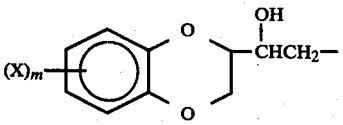

wherein X and m is as defined above, are prepared by reacting compounds of formula (VIII) with an epoxy compound of the formula:

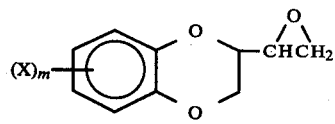

in the presence of a solvent such as toluene/methanol mixture, ethanol and dimethylformamide and the like. The reaction mixture is heated to a temperature of about 60° C. to about 150° C., preferably to about 70° C. to about 90° C. for 6 hours to about 24 hours. To obtain the erythro isomer of compounds of formula (I) the erythro isomer of the above epoxide is used in the reaction.

Alternatively, compounds of formula (I) wherein $R^1$ is group (b) above are prepared by reacting compounds of formula (VIII) with the appropriate (1,4-benzodioxan-2-yl)-α-bromomethyl ketone. The ketone intermediate that is formed is then reduced to the alcohol by methods well known in the art to yield compounds of formula (I). The erythro isomer is prepared by reducing the keto compound with a metal hydride reducing agent such as sodium borohydride or lithium tri-tert-butoxy aluminum hydride.

Another method of preparing compounds of formula (I) wherein $R^1$ is group (b) is first by reducing the α-bromo ketone to the corresponding alcohol and then reacting the alcohol with compounds of formula (VIII). The erythro isomer of the compounds of formula (I) is obtained by reducing the ketone with a metal hydride reducing agent such as sodium borohydride or lithium tri-tert-butoxy aluminum hydride to obtain the erythro isomer of the α-bromo alcohol.

The intermediate 1,4-benzodioxan-2-yl epoxide compounds are prepared by condensing unsubstituted or substituted catechol with 2,3-bis halomethyloxirane in the presence of a strong base, such as alkali metal hydroxides, alkoxides or hydrides, for example, sodium or potassium hydroxide, methoxide or hydride. The reaction is run in an inert solvent such as dimethylformamide, dimethylsulfoxide and the like at a temperature of about room temperature to about 100° C., preferably from about 50° to 70° C.

The catechols are readily available or if not readily available may be prepared by methods well known in the art. 1,4-Dihalo-2,3-epoxybutane is conveniently obtained by epoxidizing the corresponding olefin, e.g., dihalides of 1,4-but-2-ene-diols. The butene compound may be epoxidized with peracids such as perbenzoic acid, peractic acid and the like or by catalytic epoxidation using air or oxygen with a catalyst such as a silver, platinum or palladium catalyst.

The intermediate 1,4-benzodioxan-2-yl epoxide compounds can also be prepared by condensing unsubstituted or substituted salicylaldehydes or 2-hydroxyacetophenones with a 1,4-dihalo-2-butene in the presence of bases such as alkali metal hydroxides, e.g., sodium hydroxide or potassium hydroxide, or an alkali metal carbonate, e.g., sodium carbonate or potassium carbonate, in solvents such as water or ethanol. The 4-chloro-2-butenylether thus formed is reacted with a peracid such as meta-chloroperoxybenzoic acid in a solvent such as chloroform or methylene chloride at temperatures of 40° C. to 60° C. Treatment of the resulting product with an alkali metal hydroxide in a solvent mixture such as methanol/water affords the 1,4-benzodioxan-2-yl epoxide.

The (1,4-benzodioxan-2-yl)-α-bromomethyl ketones are prepared by methods well known in the art, such as is described in J. Med. Chem. 13, 169 (1970) and *Organic Chemistry*, Robert T. Morrison and Robert N. Boyd, 2nd Ed., 857–863, (1969).

The compounds of formula (I) may be isolated as free bases, but it is more convenient to isolate the compounds of the instant invention as acid addition salts. These salts are prepared in the usual manner, i.e., by reaction of the free base with a suitable organic or inorganic acid, for example, one of the pharmaceutically acceptable acids described above. The base of formula (I), dissolved in an unreactive solvent such as an alcohol, e.g., methanol and ethanol, or an ether, e.g., diethyl ether and the like, is acidified with an acid dissolved in a like solvent. The acid solution is added until precipitation of the salt is complete. The reaction is carried out at a temperature of 20° to 50° C., preferably at room temperature. If desired, the salt can be readily converted to the free base by treatment with a base such as potassium or sodium carbonate or ammonium, potassium, or sodium hydroxide.

The following specific description is given to enable those skilled in the art to more clearly understand and practice the invention. It should not be considered as a limitation upon the scope of the invention but merely as being illustrative and representative thereof.

PREPARATION 1

(Preparation of Compounds of Formula (IV) Wherein $R^2$ is Hydrogen)

In a 250 ml flask under argon was mixed 1.2 g mineral oil-free sodium hydride, 11 g trimethylsulfoxonium iodide and 60 ml dimethylsulfoxide. The mixture was stirred for two hours and then 9.32 g of N-carbobenzyloxy-4-piperidone was added. The stirring continued at room temperature for 30 minutes, at 50° for one hour, then at room temperature for 18 hours. The mixture was poured into 300 ml water and extracted with three 70 ml portions of diethyl ether. The combined diethyl ether extracts were washed with 50 ml water. Removal of solvent by evaporation afforded 3.8 g of crude 1-carbobenzoxypiperidin-4-epoxide.

PREPARATION 2

(Preparation of Compounds of Formula (IV) Wherein $R^2$ is Lower Alkyl)

(A) Butyl lithium (44 ml of 1.6 M in hexane) was added slowly to a stirred suspension of 27 g of (n-propyl)triphenylphosphonium bromide in 350 ml of tetrahydrofuran and the resulting solution was refluxed for 1 hour. The mixture was cooled in an ice bath and 18 g of N-carbobenzyloxy-4-piperidone was added. After stirring at room temperature of 0.5 hour, the solution was refluxed for 2 hours. The cooled mixture was concentrated under reduced pressure, partitioned between ether and water, and the ether layer was dried (sodium sulfate) and evaporated. The residue was filtered through silica gel with 20% ethyl acetate-hexane to give 10 g of 1-carbobenzoxy-4-(1-butylidene)piperidine as a colorless oil.

(B) The above olefin (13.3 g) in 150 ml of chloroform at 50° C. was treated with 12 g of m-chloroperoxybenzoic acid and the resulting solution was kept at 5° C. for 20 hours. The chloroform was washed with 5% sodium hydroxide solution and evaporated to afford 14 g of 1-carbobenzoxy-4,1′-epoxybutylpiperidine as a colorless oil.

(C) Similarly, proceeding as in Part A and B above, substituting the appropriate $R^2$-triphenylphosphonium bromide for (n-propyl)triphenylphosphonium bromide the following compounds are prepared:

1-carbobenzoxy-4,1′-epoxyethylpiperidine, $R^2$ is methyl;

1-carbobenzoxy-4,1′-epoxypropylpiperidine, $R^2$ is ethyl;

1-carbobenzoxy-4,1′-epoxy-2-methylpropylpiperidine, $R^2$ is i-propyl; and 1-carbobenzoxy-4,1′-epoxypentylpiperidine, $R^2$ is n-butyl.

PREPARATION 3

(A) (Preparation of Compounds of Formula (VI)):

A solution of 77 g of 1-carbobenzoxypiperidin-4-epoxide in 1 liter of 15% ammonia-methanol was heated in a steel bomb at 100° for 24 hours. The mixture was cooled and evaporated and the residue was dissolved in 600 ml of ethyl acetate. Water (500 ml) and 125 g of potassium carbonate were added and the two phase mixture was cooled to 5° C. and 35 ml of chloroacetyl chloride was slowly added. The ethyl acetate layer was separated and evaporated to a residue which was dissolved in 400 ml of acetone. Sodium iodide (75 g) was added and the solution was stirred for 12 hours at reflux. The solvent was evaporated and the residue was partitioned between water and ethyl acetate. The ethyl acetate was evaporated and the residue was filtered through 1.25 kg of silica gel with ethyl acetate eluent to afford 59.6 g of 1-carbobenzoxy-4-hydroxy-4-(1-iodoacetylamidomethyl)piperidine as a white solid; mp 115°–117° C.

(B) (Preparation of Compounds of Formula (VIII)):

A solution of potassium t-butoxide (25 g) in t-butanol (600 ml) was refluxed while a solution of 1-carbobenzoxy-4-hydroxy-4-(1-iodoacetylamidomethyl)piperidine (50 g) in tetrahydrofuran (300 ml) was slowly added. The mixture was neutralized with acetic acid, evaporated, dissolved in ethyl acetate and washed with water. Evaporation of the ethyl acetate left a residue which was triturated with ether to afford 90 g of solid. This material (70 g) was dissolved in 400 ml of 2 N HBr in acetic acid and stirred for 1 hour. The precipitate was filtered and washed with ether to give 70 g of the hydrobromide salt of 1-oxa-4,9-diazaspiro[5.5]undecan-3-one as a white solid; mp 200°–202° C.

(C) Similarly, proceeding as in Parts A and B above, but substituting methylamine, ethylamine, n-propylamine, and i-butylamine for ammonia, the following compounds are prepared:

4-methyl-1-oxa-4,9-diazaspiro[5.5]undecan-3-one;
4-ethyl-1-oxa-4,9-diazaspiro[5.5]undecan-3-one;
4-n-propyl-1-oxa-4,9-diazaspiro[5.5]undecan-3-one; and
4-i-butyl-1-oxa-4,9-diazaspiro[5.5]undecan-3-one.

(D) Similarly, proceeding as in Parts A and B above, but substituting the appropriate epoxide from Preparation 2 for 1-carbobenzoxypiperidin-4-epoxide, the following compounds are prepared:

5-methyl-1-oxa-4,9-diazaspiro[5.5]undecan-3-one;
5-ethyl-1-oxa-4,9-diazaspiro[5.5]undecan-3-one;
5-i-propyl-1-oxa-4,9-diazaspiro[5.5]undecan-3-one; and
5-n-butyl-1-oxa-4,9-diazaspiro[5.5]undecan-3-one.

(E) Similarly, proceeding as in Parts A and B above, but substituting the appropriate epoxide from Preparation 2 for 1-carbobenzyloxypiperidin-4-epoxide and methylamine, ethylamine, i-propylamine and n-butylamine for ammonia, the following compounds are prepared:

4,5-dimethyl-1-oxa-4,9-diazaspiro[5.5]undecan-3-one;
4-ethyl-5-methyl-1-oxa-4,9-diazaspiro[5.5]undecan-3-one;
5-ethyl-4-methyl-1-oxa-4,9-diazaspiro[5.5]undecan-3-one;
5-methyl-4-i-propyl-1-oxa-4,9-diazaspiro[5.5]undecan-3-one; and
4-n-butyl-5-ethyl-1-oxa-4,9-diazaspiro[5.5]undecan-3-one.

(F) Similarly, proceeding as in Part A and B above, substituting α-chloropropionyl chloride, α-chlorobutryl chloride, and α-chlorohexanoyl chloride for α-chloroacetyl chloride, the following compounds are prepared:

2-methyl-1-oxa-4,9-diazaspiro[5.5]undecan-3-one;
2-ethyl-1-oxa-4,9-diazaspiro[5.5]undecan-3-one; and
2-i-butyl-1-oxa-4,9-diazaspiro[5.5]undecan-3-one.

(G) Similarly, proceeding as in Part A and B above, but substituting the appropriate amine for ammonia and the appropriate acid chloride for α-chloroacetyl chloride, the following compounds are prepared:
2,4-dimethyl-1-oxa-4,9-diazaspiro[5.5]undecan-3-one from methylamine and α-chloropropionyl chloride;
2-ethyl-4-methyl-1-oxa-4,9-diazaspiro[5.5]undecan-3-one from methylamine and α-chlorobutryl chloride;
2-i-propyl-4-methyl-1-oxa-4,9-diazaspiro[5.5]undecan-3-one from methylamine and β-methyl-α-chlorobutryl chloride; and
2-n-butyl-4-ethyl-1-oxa-4,9-diazaspiro[5.5]undecan-3-one from ethylamine and α-chlorohexanoyl chloride.

(H) Similarly, proceeding as in Parts A and B above, but substituting the appropriate epoxide from Preparation 2 for 1-carbobenzyloxy-piperidine-4-epoxide α-chloropropionyl chloride, α-chlorobutryl chloride, and α-chlorohexanoyl chloride for α-chloroacetyl chloride, the following compounds are prepared:
2,5-dimethyl-1-oxa-4,9-diazaspiro[5.5]undecan-3-one;
2-ethyl-5-methyl-1-oxa-4,9-diazaspiro[5.5]undecan-3-one;
2-methyl-5-i-propyl-1-oxa-4,9-diazaspiro[5.5]undecan-3-one; and
2-n-butyl-5-methyl-1-oxa-4,9-diazaspiro[5.5]undecan-3-one.

PREPARATION 4

(Preparation of Compounds of Formula (IX) Wherein Y is halo)

(A) To a mechanically stirred mixture of 31 g triphenylphosphine and 375 ml acetonitrile, 18.9 g bromine is added dropwise over 20 minutes. The mixture is stirred 20 minutes at 0° and the ice bath is removed. A solution of 16 g of 2-(1,4-benzodioxan-2-yl)ethanol in 150 ml acetonitrile is added over 30 minutes. After stirring 2 hours a room temperature the mixture is diluted with 1000 ml diethyl ether. The liquid is decanted from the precipitated orange oil. The residue is washed with an additional 500 ml diethyl ether. The volume of the ethereal extracts is reduced to about 60 ml and the solution is filtered through 150 g silica gel with diethyl ether. The solvent is removed to yield 2-benzodioxan-2-yl ethyl bromide, a colorless oil, 18 g.

(B) Similarly, proceeding as in Part A above, substituting the appropriate 2-(1,4-benzodioxan-2-yl)ethanol, the following compounds are prepared.
2-(6-methyl-1,4-benzodioxan-2-yl)ethyl bromide;
2-(6-methoxy-1,4-benzodioxan-2-yl)ethyl bromide;
2-(6-chloro-1,4-benzodioxan-2-yl)ethyl bromide;
2-(7-methyl-1,4-benzodioxan-2-yl)ethyl bromide;
2-(7-methoxy-1,4-benzodioxan-2-yl)ethyl bromide;
2-(7-chloro-1,4-benzodioxan-2-yl)ethyl bromide;
2-(6,7-dimethyl-1,4-benzodioxan-2-yl)ethyl bromide;
1,4-benzodioxan-2-ylmethyl bromide; and
3-(1,4-benzodioxan-2-yl)propyl bromide.

PREPARATION 5

(Preparation of Compounds of Formula (X))

(A) To the solution of 1.32 g of catechol in 15 ml of dimethylsulfoxide 0.8 g of sodium hydroxide pellets was added while stirring under nitrogen at 55° C. After about 4 hours the dark green solution was combined with 1.5 g of trans-2,3-bis-chloromethyloxirane and stirring was continued for 4 hours at 55°-60° C. After cooling to room temperature the mixture was diluted with 100 ml of water and extracted with diethyl ether. The extract was washed with aqueous sodium hydroxide and saturated aqueous sodium chloride, dried and evaporated to yield 1.6 g of a light yellow oil. It was chromatographed on silica gel and eluated with chloroform to yield, after evaporation, 0.9 g of a colorless oil which solidified on standing. It was crystallized from diethyl ether to yield the d,l-erythro-1,4-benzodioxan-2-yl epoxide, m.p. 51°-52° C.

(B) Similarly, proceeding as in Part A above, but substituting the appropriate substituted catechol for catechol, the following compounds are prepared:
6-methyl-1,4-benzodioxan-2-yl epoxide,
6-methoxy-1,4-benzodioxan-2-yl epoxide,
6-chloro-1,4-benzodioxan-2-yl epoxide,
7-methyl-1,4-benzodioxan-2-yl epoxide,
7-methoxy-1,4-benzodioxan-2-yl epoxide,
7-chloro-1,4-benzodioxan-2-yl epoxide; and
6,7-dimethyl-1,4-benzodioxan-2-yl epoxide.

EXAMPLE 1

(Preparation of Compounds of Formula (I) Wherein $R^1$ is group (a))

(A) A solution of 1-oxa-4,9-diazaspiro[5.5]undecan-3-one (2.5 g.) and 3.0 g. of 2-(1,4-benzodioxan-2-yl)ethyl bromide in 40 ml of dimethylformamide and 10 ml of triethylamine was heated to 70° C. for 3 hours. The mixture was poured into water, extracted with methylene chloride, and the methylene chloride was extracted with aqueous HCl. The aqueous extract was made basic with ammonium hydroxide and extracted with methylene chloride and the methylene chloride layer was evaporated to give 9-[2-(1,4-benzodioxan-2-yl)ethyl]-1-oxa-4,9-diazaspiro[5.5]undecan-3-one, m.p. 139°-140° C. The base was converted to the HCl salt of 9-[2-(1,4-benzodioxan-2-yl)ethyl]-1-oxa-4,9-diazaspiro-[5.5]undecan-3-one by dissolution in methanolic HCl and precipitation with ether, m.p. 225°-227° C.

(B) Similarly, proceeding as in Part A above, but substituting the appropriate substituted-1-oxa-4,9-diazaspiro[5.5]undecan-3-one from Preparation 3 for 1-oxa-4,9-diazaspiro[5.5]undecan-3-one, the following compounds are prepared:
9-[2-(1,4-benzodioxan-2-yl)ethyl]-4-methyl-1-oxa-4,9-diazaspiro[5.5]undecan-3-one;
9-[2-(1,4-benzodioxan-2-yl)ethyl]-4-ethyl-1-oxa-4,9-diazaspiro[5.5]undecan-3-one;
9-[2-(1,4-benzodioxan-2-yl)ethyl]-4-n-propyl-1-oxa-4,9-diazaspiro[5.5]undecan-3-one;
9-[2-(1,4-benzodioxan-2-yl)ethyl]-4-i-butyl-1-oxa-4,9-diazaspiro[5.5]undecan-3-one;
9-[2-(1,4-benzodioxan-2-yl)ethyl]-5-methyl-1-oxa-4,9-diazaspiro[5.5]undecan-3-one;
9-[2-(1,4-benzodioxan-2-yl)ethyl]-5-ethyl-1-oxa-4,9-diazaspiro[5.5]undecan-3-one;
9-[2-(1,4-benzodioxan-2-yl)ethyl]-5-i-propyl-1-oxa-4,9-diazaspiro[5.5]undecan-3-one;
9-[2-(1,4-benzodioxan-2-yl)ethyl]-5-n-butyl-1-oxa-4,9-diazaspiro[5.5]undecan-3-one;
9-[2-(1,4-benzodioxan-2-yl)ethyl]-4,5-dimethyl-1-oxa-4,9-diazaspiro[5.5]undecan-3-one;
9-[2-(1,4-benzodioxan-2-yl)ethyl]-4-ethyl-5-methyl-1-oxa-4,9-diazaspiro[5.5]undecan-3-one;
9-[2-(1,4-benzodioxan-2-yl)ethyl]-5-ethyl-4-methyl-1-oxa-4,9diazaspiro[5.5]undecan-3-one;
9-[2-(1,4-benzodioxan-2-yl)ethyl]-5-methyl-4-i-propyl-1-oxa-4,9-diazaspiro[5.5]undecan-3-one;

9-[2-(1,4-benzodioxan-2-yl)ethyl]-4-n-butyl-5-ethyl-1-oxa-4,9-diazaspiro[5.5]undecan-3-one;

9-[2-(1,4-benzodioxan-2-yl)ethyl]-2-methyl-1-oxa-4,9-diazaspiro[5.5]undecan-3-one;

9-[2-(1,4-benzodioxan-2-yl)ethyl]-2-ethyl-1-oxa-4,9-diazaspiro[5.5]undecan-3-one;

9-[2-(1,4-benzodioxan-2-yl)ethyl]-2-i-butyl-1-oxa-4,9-diazaspiro[5.5]undecan-3-one;

9-[2-(1,4-benzodioxan-2-yl)ethyl]-2,4-dimethyl-1-oxa-4,9-diazaspiro[5.5]undecan-3-one;

9-[2-(1,4-benzodioxan-2-yl)ethyl]-2-ethyl-4-methyl-1-oxa-4,9-diazaspiro[5.5]undecan-3-one;

9-[2-(1,4-benzodioxan-2-yl)ethyl]-2-i-propyl-4-methyl-1-oxa-4,9-diazaspiro[5.5]undecan-3-one;

9-[2-(1,4-benzodioxan-2-yl)ethyl]-2-n-butyl-4-ethyl-1-oxa-4,9-diazaspiro[5.5]undecan-3-one;

9-[2-(1,4-benzodioxan-2-yl)ethyl]-2,5-dimethyl-1-oxa-4,9-diazaspiro[5.5]undecan-3-one;

9-[2-(1,4-benzodioxan-2-yl)ethyl]-2-ethyl-5-methyl-1-oxa-4,9-diazaspiro[5.5]undecan-3-one;

9-[2-(1,4-benzodioxan-2-yl)ethyl]-2-methyl-5-i-propyl-1-oxa-4,9-diazaspiro[5.5]undecan-3-one; and 9-[2-(1,4-benzodioxan-2-yl)ethyl]-2-n-butyl-5-methyl-1-oxa-4,9-diazaspiro[5.5]undecan-3-one.

(C) Similarly, proceeding as in Part A above, but substituting the appropriate 1,4-benzodioxan-2-ylalkyl bromide from Preparation 4 for 2-(1,4-benzodioxan-2-yl)ethyl bromide, the following compounds are prepared:

9-[2-(6-methyl-1,4-benzodioxan-2-yl)ethyl]-1-oxa-4,9-diazaspiro[5.5]undecan-3-one;

9-[2-(6-methoxy-1,4-benzodioxan-2-yl)ethyl]-1-oxa-4,9-diazaspiro[5.5]undecan-3-one;

9-[2-(6-chloro-1,4-benzodioxan-2-yl)ethyl]-1-oxa-4,9-diazaspiro[5.5]undecan-3-one;

9-[2-(7-methyl-1,4-benzodioxan-2-yl)ethyl]-1-oxa-4,9-diazaspiro[5.5]undecan-3-one;

9-[2-(7-methoxy-1,4-benzodioxan-2-yl)ethyl]-1-oxa-4,9-diazaspiro[5.5]undecan-3-one;

9-[2-(7-chloro-1,4-benzodioxan-2-yl)ethyl]-1-oxa-4,9-diazaspiro[5.5]undecan-3-one;

9-[2-(6,7-dimethyl-1,4-benzodioxan-2-yl)ethyl]-1-oxa-4,9-diazaspiro[5.5]undecan-3-one;

9-(1,4-benzodioxan-2-ylmethyl)-1-oxa-4,9-diazaspiro[5.5]undecan-3-one, hydrochloride salt, m.p. 164°–166° C.; and 9-[3-(1,4-benzodioxan-2-yl)propyl]-1-oxa-4,9-diazaspiro[5.5]undecan-3-one.

EXAMPLE 2

(Preparation of Compounds of formula (I) wherein $R^1$ is group (b))

(A) A solution of 0.70 g. of 4-methyl-1-oxa-4,9-diazaspiro[5.5]undecan-3-one and 0.71 g. of the erythro-1,4-benzodioxan-2-yl epoxide in 20 ml of toluene and 20 ml of methanol was refluxed for 12 hours. Evaporation and chromatography of the residue on silica gel with 10% methanol-methylene chloride gave 0.5 g. of erythro-9-[2-(1,4-benzodioxan-2-yl)-2-hydroxyethyl]-4-methyl-1-oxa-4,9-diazaspiro[5.5]undecan-3-one. Erythro-9-[2-(1,4-benzodioxan-2-yl)-2-hydroxyethyl]-4-methyl-1-oxa-4,9-diazaspiro[5.5]undecan-3-one was dissolved in methanolic HCl and precipitated with ether to give the HCl salt, m.p. 211°–213° C.

(B) Similarly, proceeding as in Part A above, but substituting the appropriate substituted 1-oxa-4,9-diazaspiro[5.5]undecan-3-one from Preparation 3 for 4-methyl-1-oxa-4,9-diazaspiro[5.5]undecan-3-one, the following compounds are prepared:

erythro-9-[2-(1,4-benzodioxan-2-yl)-2-hydroxyethyl]-1-oxa-4,9-diazaspiro[5.5]undecan-3-one, hydrochloride salt, m.p. 177°–180° C.;

9-[2-(1,4-benzodioxan-2-yl)-2-hydroxyethyl]-4-ethyl-1-oxa-4,9-diazaspiro[5.5]undecan-3-one;

9-[2-(1,4-benzodioxan-2-yl)-2-hydroxyethyl]-4-n-propyl-1-oxa-4,9-diazaspiro[5.5]undecan-3-one;

9-[2-(1,4-benzodioxan-2-yl)-2-hydroxyethyl]-4-i-butyl-1-oxa-4,9-diazaspiro[5.5]undecan-3-one;

9-[2-(1,4-benzodioxan-2-yl)-2-hydroxyethyl]-5-methyl-1-oxa-4,9-diazaspiro[5.5]undecan-3-one;

erythro-9-[2-(1,4-benzodioxan-2-yl)-2-hydroxyethyl]-5-ethyl-1-oxa-4,9-diazaspira[5.5]undecan-3-one, hydrochloride salt, m.p. 263°–266° C.;

9-[2-(1,4-benzodioxan-2-yl)-2-hydroxyethyl]-5-i-propyl-1-oxa-4,9-diazaspiro[5.5]undecan-3-one;

9-[2-(1,4-benzodioxan-2-yl)-2-hydroxyethyl]5-n-butyl-1-oxa-4,9-diazaspiro[5.5]undecan-3-one;

9-[2-(1,4-benzodioxan-2-yl)-2-hydroxyethyl]-4,5-dimethyl-1-oxa-4,9-diazaspiro[5.5]undecan-3-one;

9-[2-(1,4-benzodioxan-2-yl)-2-hydroxyethyl]-4-ethyl-5-methyl-1-oxa-4,9-diazaspiro[5.5]undecan-3-one;

9-[2-(1,4-benzodioxan-2-yl)-2-hydroxyethyl]-5-ethyl-4-methyl-1-oxa-4,9-diazaspiro[5.5]undecan-3-one;

9-[2-(1,4-benzodioxan-2-yl)-2-hydroxyethyl]-5-methyl-4-i-propyl-1-oxa-4,9-diazaspiro[5.5]undecan-3-one;

9-[2-(1,4-benzodioxan-2-yl)-2-hydroxyethyl]-4-n-butyl-5-ethyl-1-oxa-4,9-diazaspiro[5.5]undecan-3-one;

9-[2-(1,4-benzodioxan-2-yl)-2-hydroxyethyl]-2-methyl-1-oxa-4,9-diazaspiro[5.5]undecan-3-one;

9-[2-(1,4-benzodioxan-2-yl)-2-hydroxyethyl]-2-ethyl-1-oxa-4,9-diazaspiro[5.5]undecan-3-one;

9-[2-(1,4-benzodioxan-2-yl)-2-hydroxyethyl]-2-i-butyl-1-oxa-4,9-diazaspiro[5.5]undecan-3-one;

9-[2-(1,4-benzodioxan-2-yl)-2-hydroxyethyl]-2,4-dimethyl-1-oxa-4,9-diazaspiro[5.5]undecan-3-one;

9-[2-(1,4-benzodioxan-2-yl)-2-hydroxyethyl]-2-ethyl-4-methyl-1-oxa-4,9-diazaspiro[5.5]undecan-3-one;

9-[2-(1,4-benzodioxan-2-yl)-2-hydroxyethyl]-2-i-propyl-4-methyl-1-oxa-4,9-diazaspiro[5.5]undecan-3-one;

9-[2-(1,4-benzodioxan-2-yl)-2-hydroxyethyl]-2-n-butyl-4-ethyl-1-oxa-4,9-diazaspiro[5.5]undecan-3-one;

9-[2-(1,4-benzodioxan-2-yl)-2-hydroxyethyl]-2,5-dimethyl-1-oxa-4,9-diazaspiro[5.5]undecan-3-one;

9-[2-(1,4-benzodioxan-2-yl)-2-hydroxyethyl]-2-ethyl-5-methyl-1-oxa-4,9-diazaspiro[5.5]undecan-3-one;

9-[2-(1,4-benzodioxan-2-yl)-2-hydroxyethyl]-2-methyl-5-i-propyl-1-oxa-4,9-diazaspiro[5.5]undecan-3-one; and 9-[2-(1,4-benzodioxan-2-yl)-2-hydroxyethyl]-2-n-butyl-5-methyl-1-oxa-4,9-diazaspiro[5.5]undecan-3-one.

(C) Similarly, proceeding as in Part A above, but substituting the appropriate substituted 1,4-benzodioxan-2-yl epoxide for 1,4-benzodioxan-2-yl epoxide, the following compounds are prepared:

9-[2-(6-methyl-1,4-benzodioxan-2-yl)-2-hydroxyethyl]-1-oxa-4,9-diazaspiro[5.5]undecan-3-one;

9-[2-(6-methoxy-1,4-benzodioxan-2-yl)-2-hydroxyethyl]-1-oxa-4,9-diazaspiro[5.5]undecan-3-one;

9-[2-(6-chloro-1,4-benzodioxan-2-yl)-2-hydroxyethyl]-1-oxa-4,9-diazaspiro[5.5]undecan-3-one;

9-[2-(7-methyl-1,4-benzodioxan-2-yl)-2-hydroxyethyl]-1-oxa-4,9-diazaspiro[5.5]undecan-3-one;

9-[2-(7-methoxy-1,4-benzodioxan-2-yl)-2-hydroxyethyl]-1-oxa-4,9-diazaspiro[5.5]undecan-3-one;

9-[2-(7-chloro-1,4-benzodioxan-2-yl)-2-hydroxyethyl]-1-oxa-4,9-diazaspiro[5.5]undecan-3-one; and
9-[2-(6,7-dimethyl-1,4-benzodioxan-2-yl)-2-hydroxyethyl]-1-oxa-4,9-diazaspiro[5.5]undecan-3-one.

EXAMPLE 3

8.0 g of 9-[2-(1,4-benzodioxan-2-yl)ethyl]-1-oxa-4,9-diazaspiro[5.5]undecan-3-one was dissolved in methanol and acidified with methanolic hydrochloric acid. The precipitate was washed with ether to give 7.0 g of the hydrochloride salt of 9-[2-(1,4-benzodioxan-2-yl)ethyl]-1-oxa-4,9-diazaspiro[5.5]undecan-3-one, m.p. 225°–227° C. (dec).

In similar manner, all compounds of formula (I) in base form prepared in accordance with Examples 1 and 2 can be converted to their pharmaceutically acceptable acid addition salts by treatment with the appropriate acid, for example, hydrobromic acid, sulfuric acid, nitric acid, phosphoric acid, acetic acid, propionic acid, glycolic acid, pyruvic acid, oxalic acid, malonic acid, succinic acid, malic acid, maleic acid, fumaric acid, tartaric acid, citric acid, benzoic acid, cinnamic acid, mandelic acid, methansulfonic acid, ethanesulfonic acid, p-toluenesulfonic acid and the like.

EXAMPLE 4

A solution of 3.5 g of 9-[2-(1,4-benzodioxan-2-yl)ethyl]-1-oxa-4,9-diazaspiro[5.5]undecan-3-one hydrochloride salt in water (50 ml) was adjusted to pH 12 with ammonium hydroxide solution and extracted with methylene chloride. The methylene chloride was evaporated to afford 3 g of 9-[2-(1,4-benzodioxan-2-yl)ethyl]-1-oxa-4,9-diazaspiro-[5.5]undecan-3-one as the free base, mp 139°–140° C.

EXAMPLE 5

The following example illustrates the preparation of representative pharmaceutical formulations containing an active compound of Formula (I), e.g., 9-[2-(1,4-benzodioxan-2-yl)ethyl]-1-oxa-4,9-diazaspiro[5.5]undecan-3-one or 9-[2-(1,4-benzodioxan-2-yl)-2-hydroxyethyl]-1-oxa-4,9-diazaspiro[5.5]undecan-3-one.

| I.V. Formulation | |
|---|---|
| Active compound | 0.14 g |
| Propylene glycol | 20 g |
| Polyethylene glycol 400 | 20 g |
| Tween 80 | 1 g |
| 0.9% Saline solution | 100 ml |

The active compound is dissolved in propylene glycol, polyethylene glycol 400 and Tween 80. A sufficient quantity of 0.9% saline solution is then added with stirring to provide 100 ml of the I.V. solution which is filtered through a 0.2 micron membrane filter and packaged under sterile conditions.

| TABLET FORMULATION | parts by weight |
|---|---|
| Active compound | 50.0 |
| Magnesium stearate | 0.75 |
| Starch | 0.75 |
| Lactose | 29.0 |
| PVP (polyvinylpyrrolidone) | 0.75 |

The above ingredients are combined and granulated using methanol as the solvent. The formulation is then dried and formed into tablets (containing 50 mg of active compound) with an appropriate tabletting machine.

What is claimed is:

1. A compound of the formula:

wherein: $R^1$ is $R^2$, $R^3$, and $R^4$ are independently hydrogen or lower alkyl of one to four carbon atoms;
X is hydrogen, lower alkyl of one to four carbon atoms, lower alkoxy of one to four carbon atoms or halo;
m is 1 or 2; and
n is 1, 2 or 3; and
and the pharmaceutically acceptable acid addition salts thereof.

2. A compound of claim 1 of the formula:

wherein:
$R^2$, $R^3$ and $R^4$ are independently hydrogen or lower alkyl of one to four carbon atoms;
X is hydrogen, lower alkyl of one to four carbon atoms, lower alkoxy of one to four carbon atoms or halo;
m is 1 or 2; and
n is 1, 2 or 3; and
the pharmaceutically acceptable acid additions salts thereof.

3. A compound of claim 2 wherein $R^4$ is hydrogen and $R^2$ and $R^3$ are independently hydrogen or lower alkyl of one to four carbon atoms.

4. A compound of claim 3 wherein $R^2$ and $R^3$ are independently hydrogen.

5. A compound of claim 4 wherein $R^2$, $R^3$, $R^4$ and X are each hydrogen and n is 1 which is 9-(1,4-benzodioxan-2-yl-methyl)-1-oxa-4,9-diazaspiro[5.5]undecan-3-one and the pharmaceutically acceptable acid addition salts thereof.

6. A compound of claim 4 wherein $R^2$, $R^3$, $R^4$ and X are each hydrogen and n is 2 which is 9-[2-(1,4-benzodioxan-2-yl)ethyl]-1-oxa-4,9-diazaspiro[5.5]undecan-3-one and the pharmaceutically acceptable acid addition salts thereof.

7. A compound of claim 1 of the formula:

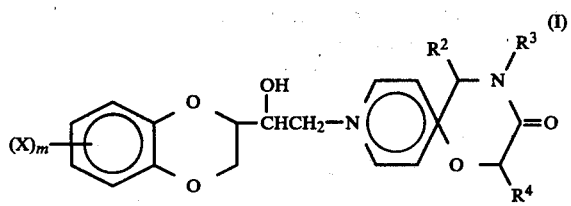

wherein:
R$^2$, R$^3$ and R$^4$ are independently hydrogen or lower alkyl of one to four carbon atoms;
X is hydrogen, lower alkyl of one to four carbon atoms, lower alkoxy of one to four carbon atoms or halo;
m is 1 or 2; and
the pharmaceutically acceptable acid addition salts thereof.

8. A compound of claim 7 wherein R$^4$ is hydrogen and R$^2$ and R$^3$ are independently hydrogen or lower alkyl of one to four carbon atoms.

9. A compound of claim 8 wherein R$^2$, R$^4$ and X are each hydrogen, and R$^3$ is methyl which is erythro-9-[2-(1,4-benzodioxan-2-yl)-2-hydroxyethyl]-4-methyl-1-oxa-4,9-diazaspiro[5.5]undecan-3-one and the pharmaceutically acceptable acid addition salts thereof.

10. A compound of claim 8 wherein R$^2$ and X are each hydrogen, and R$^3$ is ethyl which is erythro-9-[2-(1,4-benzodioxan-2-yl)-2-hydroxyethyl]-5-ethyl-1-oxa-4,9-diazaspiro[5.5]undecan-3-one and the pharmaceutically acceptable acid addition salts thereof.

11. A compound of claim 8 wherein R$^2$ and R$^3$ are independently hydrogen.

12. A compound of claim 11 wherein R$^2$, R$^3$, R$^4$ and X are each hydrogen which is erythro-9-[2-(1,4-benzodioxan-2-yl)-2-hydroxyethyl]-1-oxa-4,9-diazaspiro[5.5]undecan-3-one and the pharmaceutically acceptable acid addition salts thereof.

13. A pharmaceutical composition comprising 5 to 95% by weight of a compound of the formula:

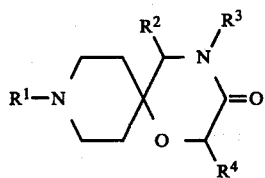

or a pharmaceutically acceptable acid addition salt thereof, wherein:
R$^1$ is:

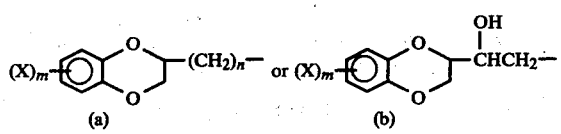

R$^2$, R$^3$, and R$^4$ are independently hydrogen or lower alkyl of one to four carbon atoms;
X is hydrogen, lower alkyl of one to four carbon atoms, lower alkoxy of one to four carbon atoms or halo;
m is 1 or 2; and
n is 1, 2 or 3; and
the pharmaceutically acceptable acid addition salts thereof in admixture with 95 to 5% of a pharmaceutically acceptable, non-toxic carrier.

14. A method for treating and/or preventing hypertension, congestive heart failure, arrhythmia, migraine, vasospastic disorders and asthma in a mammalian subject comprising administering to said subject a therapeutically effective amount of a compound of the formula:

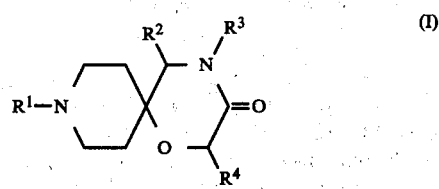

or a pharmaceutically acceptable acid addition salt thereof, wherein:
R$^1$ is:

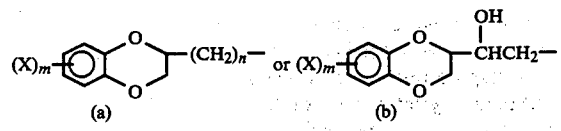

R$^2$, R$^3$, and R$^4$ are independently hydrogen or lower alkyl of one to four carbon atoms;
X is hydrogen, lower alkyl of one to four carbon atoms, lower alkoxy of one to four carbon atoms or halo;
m is 1 or 2; and
n is 1, 2 or 3; and
the pharmaceutically acceptable acid addition salts thereof or a pharmaceutical composition containing such compound as an active ingredient.

15. A method of claim 1 for treating and/or preventing hypertension in a mammalian subject.

* * * * *